United States Patent

Dixon et al.

[11] Patent Number: 5,944,703
[45] Date of Patent: Aug. 31, 1999

[54] WOUND DRAINAGE SYSTEM

[75] Inventors: Michael Dixon, Fremantle; Raymond Lawrence Stubber, Sorrento, both of Australia

[73] Assignee: Research Medical Pty Ltd., Leadersville, Australia

[21] Appl. No.: 08/817,497

[22] PCT Filed: Oct. 11, 1995

[86] PCT No.: PCT/AU95/00674

§ 371 Date: Apr. 10, 1997

§ 102(e) Date: Apr. 10, 1997

[87] PCT Pub. No.: WO96/11031

PCT Pub. Date: Apr. 18, 1996

[30] Foreign Application Priority Data

Oct. 11, 1994 [AU] Australia ............................... PM 8712
Jan. 4, 1995 [AU] Australia ............................... PO 0386

[51] Int. Cl.⁶ ..................................................... A61M 1/00
[52] U.S. Cl. ........................... 604/319; 604/317; 604/320
[58] Field of Search ................................... 604/118, 119, 604/317, 319, 320, 321

[56] References Cited

U.S. PATENT DOCUMENTS

| 3,086,528 | 4/1963 | Eichelman | 128/276 |
|---|---|---|---|
| 3,659,605 | 5/1972 | Sielaff | 128/276 |
| 3,830,238 | 8/1974 | Kurtz | 128/275 |
| 4,303,072 | 12/1981 | Lewis | 128/276 |
| 4,681,571 | 7/1987 | Nehring | 604/320 |
| 4,718,895 | 1/1988 | Kurtz | 604/119 |
| 5,073,172 | 12/1991 | Fell | 604/119 |
| 5,423,780 | 6/1995 | Malette | 604/317 |

FOREIGN PATENT DOCUMENTS

| A-19675/83 | 4/1984 | Australia . |
| B-32844/93 | 4/1993 | Australia . |
| 0 113 541 A2 | 7/1984 | European Pat. Off. . |
| 2560770 | 9/1985 | France . |
| 2077600 | 12/1981 | United Kingdom . |
| WO 88/05319 | 7/1988 | WIPO . |

*Primary Examiner*—John G. Weiss
*Assistant Examiner*—David J. Cho
*Attorney, Agent, or Firm*—Woodcock Washburn Kurtz Mackiewicz & Norris LLP

[57] ABSTRACT

A method and apparatus for withdrawing fluid from a wound comprising providing a passage between the wound and a collection container with a valve therebetween to control flow of fluid from the passage to the container. Cyclically establishing in the passage a level of vacuum at a selected value higher than the level of vacuum in the container to thereby draw fluid from the wound while the valve is closed to collect the fluid in the passage. The valve is opened in response to the level of vacuum in the passage falling below the select value, as a result of the buildup of fluid therein, to permit discharge of fluid from the passage into the container. As a result of the discharge of fluid, the selected level of vacuum in the passage is reestablished.

10 Claims, 5 Drawing Sheets

WOUND DRAINAGE SYSTEM

FIELD OF THE INVENTION

This invention relates to a closed wound drainage system where sub-atmospheric pressure (partial vacuum) is employed to assist the drainage. The function of wound drainage is to promote rapid and efficient healing of post-operative wounds.

BACKGROUND OF THE INVENTION

A wide range of equipment has been proposed to assist in the draining of fluid from wounds, particularly wounds resulting from surgery or accidents. One type of known construction employs a bellows type container that can be reduced in volume against the pressure of internal springs or by the force of deformation of the container material to provide a vacuum source.

These types of construction exhibit several major limitations one being that to achieve the desired level of vacuum, the container must have a high degree of resilience to develop a vacuum of the order of several pounds per square inch. This is somewhat impractical in terms of cost effective manufacture and it is not possible to effectively control or maintain the desired vacuum level for efficient drainage. Further, as only a small degree of vacuum can be created, it dissipates rapidly as the container fills with fluid. Also, it is normally very difficult, if not impossible, to monitor accurately the rate at which the fluid is collected.

Another known type of equipment for the extraction and collection of wound fluid employs a disposable container connected to a re-useable electronically driven pump, and thus require elaborate and expensive electronics, a pump and rechargeable batteries or a power supply. The inherent complexities of this type of device entails significant additional cost for initial purchase and for maintenance of the pump and controller. While the fluid containers are disposable, special provisions must be made to ensure that the non-disposable components, such as the pump assembly, are protected from contamination by the drained wound fluid.

Yet a further known type of wound fluid collector is that employing a pre-evacuated container which use volatile liquids such as pentane and hexane to achieve the required level of vacuum. However these do not provide a capability to vary or otherwise control the level of vacuum, and if a leak occurs which dissipates the vacuum there is no ability to re-establish the vacuum. These systems often operate at a higher degree of vacuum than is ideally desired for optimum drainage in many situations.

There is a variant of this latter form of wound fluid collector which use an elaborate, separate, non-adjustable regulator of the flexible throttled tube type which can be attached to the drain bottle. This does help to avoid an overly strong suction, but still has the other shortcomings of the non-regulated system and additionally there is the substantial added cost of the regulator, which cannot be re-used for another patient, as the regulator becomes contaminated by the drained wound fluids during use.

OBJECTS OF THE INVENTION

The object of this invention is to provide an improved method and apparatus for effecting closed wound drainage especially in regard to a cost effectiveness, disposability, and reliability and simplicity in operation.

SUMMARY OF THE INVENTION

There is thus provided in one embodiment a method of withdrawing fluid from a wound comprising providing a passage between the wound and a container with valve means to control flow of fluid from the passage to the container, said method comprising cyclically establishing in the passage a level of vacuum at or above a selected value and a higher level of vacuum in the container, drawing fluid from the wound while the valve means is closed to collect said fluid in said passage, and opening said valve means in response to the level of vacuum in said passage falling below said select value to permit discharge of fluid from said passage to the container to thereby re-establish said selected or higher level of vacuum in the passage.

Preferably, the level of vacuum is maintained in the container is greater than that existing in the passage and the opening of the valve means establishes a fluid flow from the passage through the valve means into the container to remove fluid from the passage and so maintain the desired level of vacuum in the passage.

Conveniently the level of vacuum to be maintained in the passage is selectable within a desired preset range.

There is also provided in another embodiment an apparatus for withdrawing fluid from a wound comprising a conduit to be connected at one end to a wound to receive fluid from the wound and to deliver said fluid to a container, and valve means to in use selectively provide communication between the conduit and container, said valve means being adopted to establish communication between the conduit and the container in response to the existence of a level of vacuum in said conduit below a selected value.

Conveniently, the valve means is adjustable to respond to a level of vacuum between zero to a chosen maximum degree of vacuum thereby enabling the level of vacuum in the conduit to be adjusted to suit the prevailing wound condition.

Preferably, the valve means is operated by a diaphragm means exposed to atmospheric pressure on one side and to the level of vacuum exists in the conduit on the other side. An adjustable force means may be arranged to apply a force to the diaphragm in opposition to the atmospheric pressure. The difference between the force applied by the adjustable force means and the force generated by the atmospheric pressure is the force required to be applied by the level of vacuum in the conduit to close the valve means to interrupt communication between the container and the conduit, and consequently the level of vacuum existing to promote withdrawal of fluid from the wound.

Thus variations in the extent of the force applied by the adjustable force means controls the level of vacuum in the conduit that effects withdraw the fluid from the wound. The higher the force applied by the adjustable force means, in opposition to the force of atmospheric pressure on the diaphragm, the lower is the sub-atmospheric pressure maintained in the conduit to withdraw wound fluid, and vice versa.

The invention will be more readily understood from the following description of one practical arrangement of the wound drainage system and apparatus as illustrated in the accompanying drawings.

DETAILED DESCRIPTION OF THE EMBODIMENT

Figure 1:
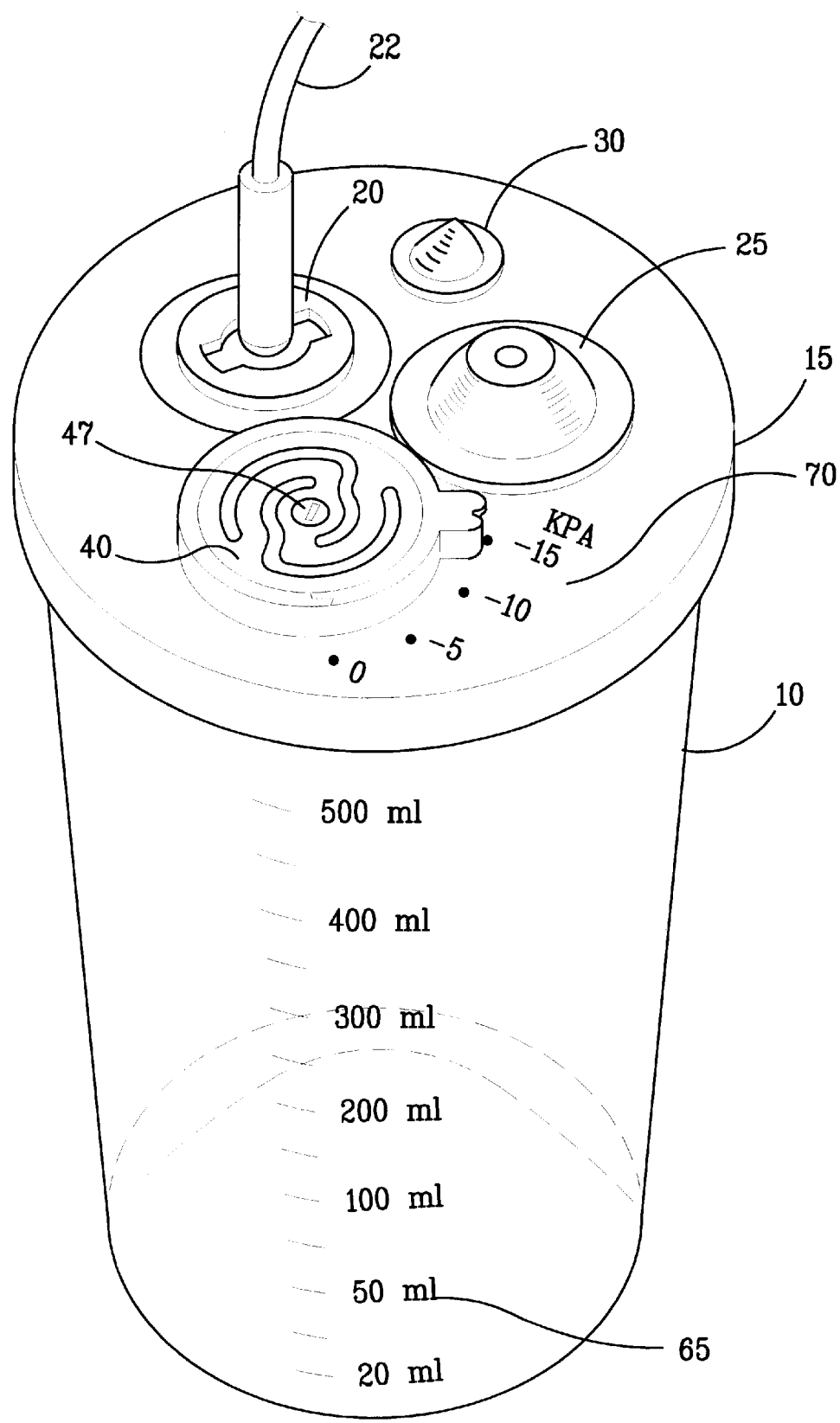
FIG. 1 is an isometric view of the overall configuration of the wound draining device.
Figure 2:
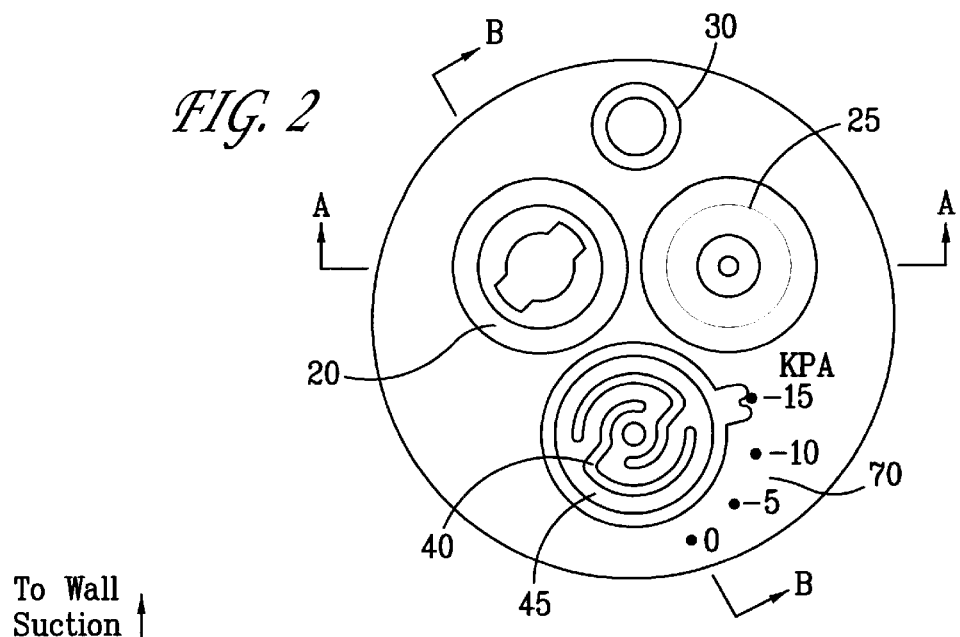
FIG. 2 is a plan view of the top of the draining device.

The drainage system includes a drainage container 10 with a cap 15 in which the functional components of the system are incorporated. The functional components include a drain tube 22, the free end (not shown) of which in use communicates with the wound site in the known conventional manner, is connected at the other end by a bayonet type fitting 20 to the cap 15 of the container 10 and incorporates a check valve 35 that will not permit flow outward from the container 10 into the tube 22.

The tube 50 within the container 10 extends from the check valve 35 to the underside of the regulator valve 40. The spigot 25, incorporating a further check valve 26, is provided for connection to a conventional in situ hospital vacuum system, thereby enabling evacuation of the drainage container 10. The resilient cone 30 functions as a diaphragm to be defected into the container 10 to visually indicate the presence of at least partial vacuum in the container 10.

Figure 4:
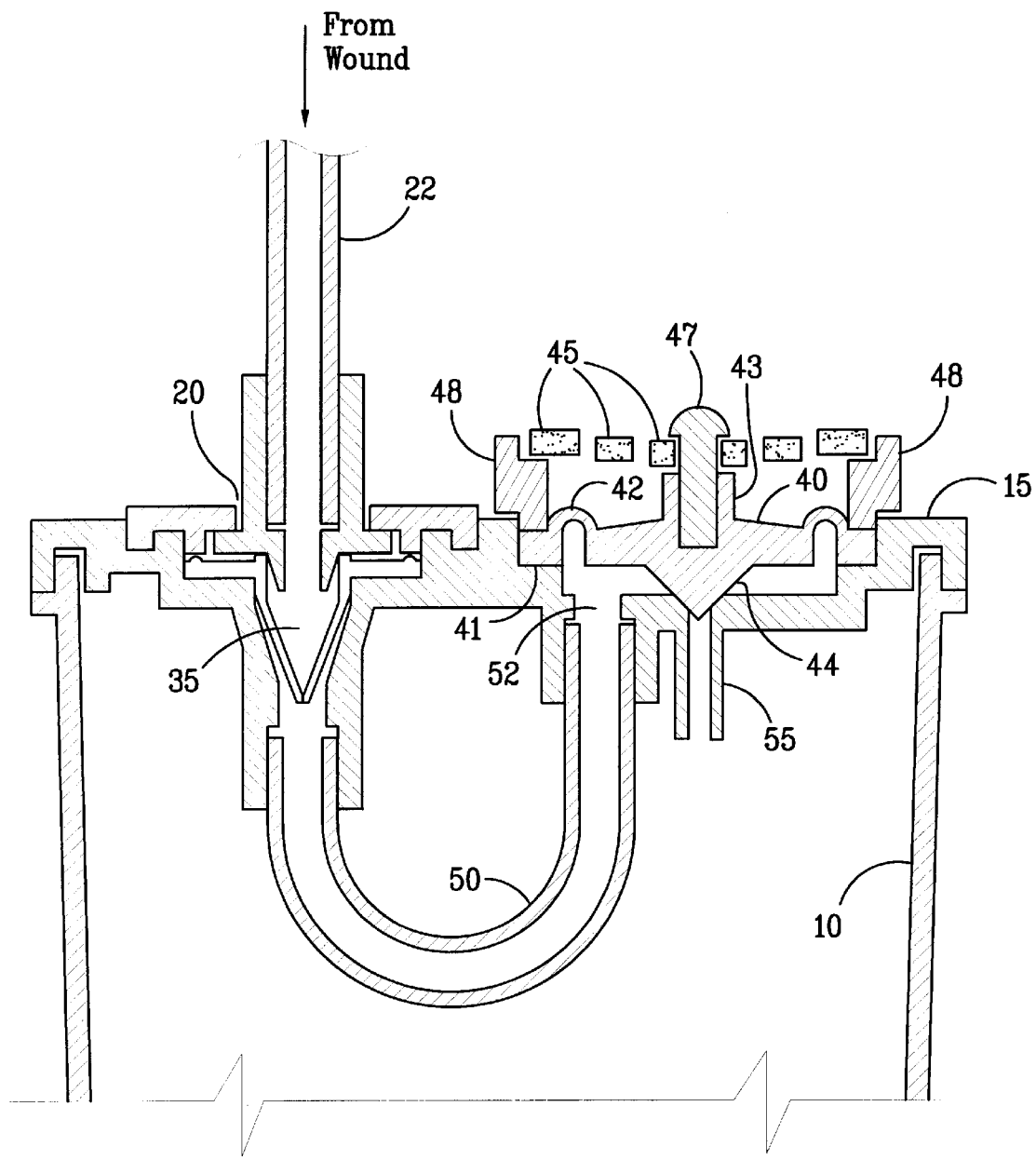
FIG. 4 is a partial section on line 3—3 of FIG. 2.

Referring to FIG. 4, the regulator valve 40 consists of a moulded elastomer disc sealably secured at the perimeter 41 thereof to the cap, and has a concentric annular compliant section 42 a threaded boss 43 at the centre of the upper face, and a central valve section 44 on the lower face. In the free position of the regulator valve 40 the valve section 44 will engage the seat 63 in the upper end of the drain tube 50 to close the tube. Above the regulator valve 40 is a rotatable compliant or resilient element 45 which when rotated will adjust the force applied to the regulator 40, in opposition to atmospheric pressure applied externally thereto.

The magnitude of force applied by the compliant element 45 is selectively adjustable by a rotational movement of the compliant element 45 in the peripheral support 48 thereof. The degree of rotation is indicated by markings 70, resulting in an indication of the up force applied to the regulator 40. The higher the force applied by the compliant element 45, the higher the level of vacuum maintained in the tube 50. This level can be further varied through the use of different grades of compliant component for different applications of the drainage system.

When wound fluid is aspirated through the tube 50 to the underside of the regulator valve 40, it is then vented through the spigot 55 into the interior of the drain container 10. The drain container has an inverted conical base 60, which allows for an expanded vertical scale of the level indicator 65 for more accurate measurement of the initial flow of wound fluid. The inverted conical shape is also advantageous in that it improves the resistance of the container to deformation due to the presence of vacuum therein.

It is well established from clinical practice that healing of post-operative wounds is assisted by proper drainage of excess fluid from within the wound site. The ideal degree of suction to be applied will vary from case to case and from time to time during the healing process. However, it can be said that the degree of suction is generally agreed to desirable lie in the range between zero and 15 kPa below atmospheric pressure.

Wall mounted reticulated vacuum systems commonly provided in hospitals are typically set between 65 and 80 kPa below atmospheric pressure (101.3 kPa), which is much too strong a suction to be used for continuous wound drainage.

The level of vacuum to be applied to the wound site by the presently proposed system is controllable through the regulator valve 40, which controls the pressure level in the wound drain tube 22. The pressure in the drainage container 10 and at the point where the spigot tube 55 meets the valve seat 63 will typically be around 70 kPa below atmospheric, immediately after evacuation by the hospital reticulated vacuum system. As the regulator valve 40 in this state is closed, no fluid can flow until there is an upward force applied to the regulator valve 40.

If gravity drainage without suction assistance is required, the upward force applied to the regulator valve can be set to zero. Independent of the degree of vacuum in the container 10, any pressure rise in the drain line 22, due to newly produced wound fluid, will be sufficient to crack the valve seal 44 and allow fluid to flow into the container through the drain spigot tube 55.

Where suction assistance is required, this is achieved by the compliant element 45, secured to the boss 43 of the regulator valve 40 by a screw 47, which is induced to flex by rotation against a circular ramp 48. The degree of flex induced is related to the degree of rotation, and can be read against the calibrated scale 70. The upward force resulting from the flexion of the compliant member 45 cracks the regulator valve 40, breaking the seal of the valve seat 44 and allowing fluid to be drawn through the spigot tube 55 into the drain container 10, thereby lowering the pressure in the area below the regulator valve, and through the orifice 52, equally lowering the pressure in the connecting tube 50 and the drain tube 22.

As fluid is passed into the drainage container 10, the pressure will reduce until a level is reached where the downward force on the lower surface of the regulator valve 40 opposing the upward flexion force applied by the compliant element 45, reaches a point of equilibrium. The regulator valve 40 will then return to its closed position. The regulator valve needs only to move small fractions of a millimetre in the transition between closed and open.

The state of equilibrium where the valve is closed can only be disturbed by either changing the upward force applied to the regulator valve 40 by the compliant element 45, thereby requiring an increased level of vacuum in the system to restore equilibrium, or by the production of a flow of wound fluid into the drain tube 22. The added volume of fluid will dissipate the level of vacuum in the drain line 22 and connecting tube 50, hence lowering the downward force on the regulator valve 40. This in turn will allow flow of wound fluid into the drain container 10, thereby increasing the level of vacuum until equilibrium is again restored.

As fluid flows into the drain container 10, the level of vacuum therein will gradually dissipate. A container of 600 mls, evacuated to minus 75 kPa, will, after draining 400 mls of wound fluid will fall to minus 10 kPa, and upon draining 450 mls the vacuum will completely dissipated.

The regulated level of vacuum in the drain line 22 is controlled by the effective size of the regulator disc 42 measured at the centre line of the annular compliant element 45 and the consequent force applied from a given pressure differential, balanced against the degree of force applied by the compliant element 45. The regulated pressure will not be adversely influenced by variation in the level of vacuum in the drain container 10 if the cross sectional area of the spigot tube 55 is kept to less than 2% of the effective area of the regulator disc 42.

Figure 5:
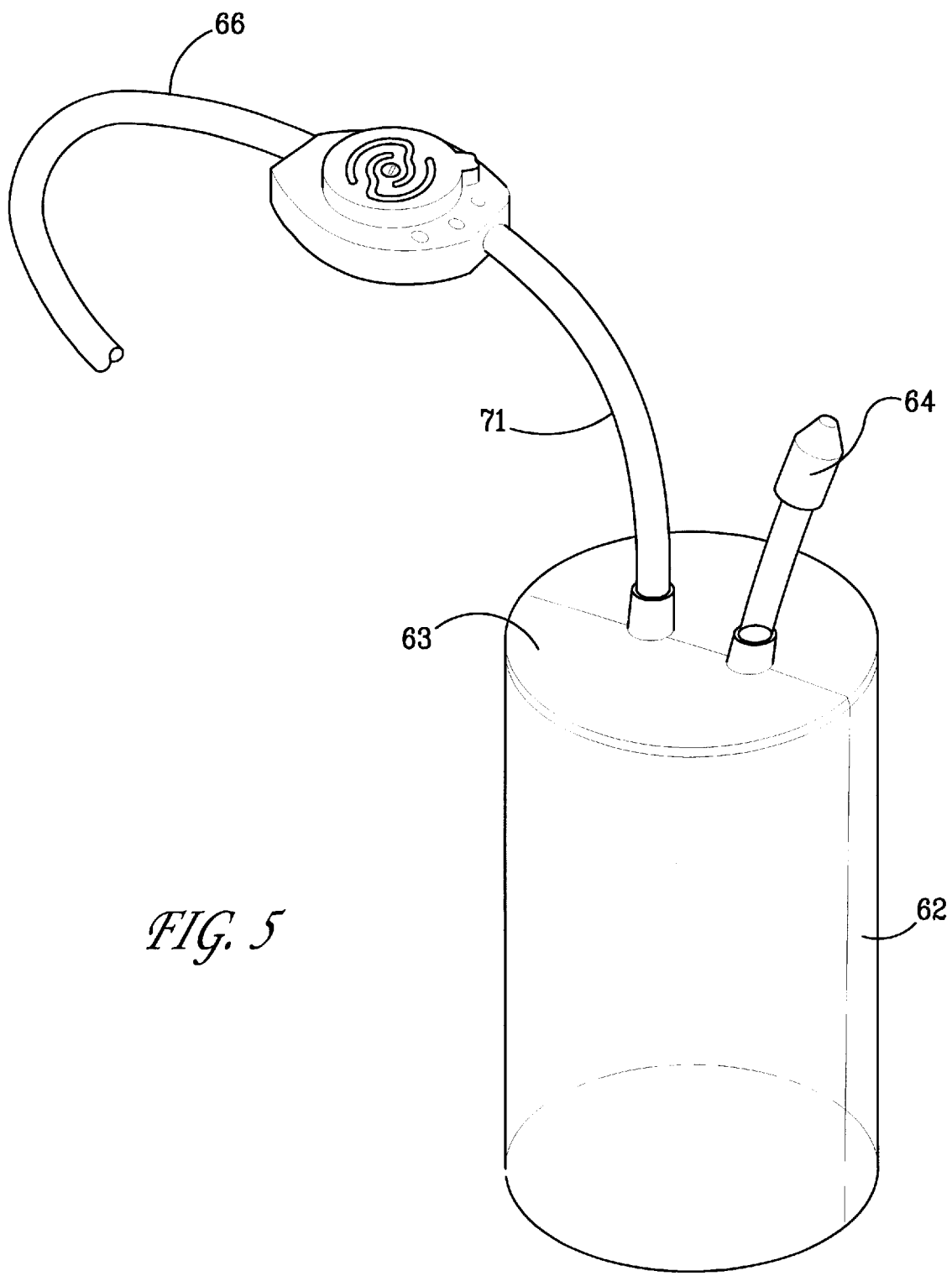
FIG. 5 is an isometric view of the overall configuration of an alternative arrangement of the draining device.
Figure 6:
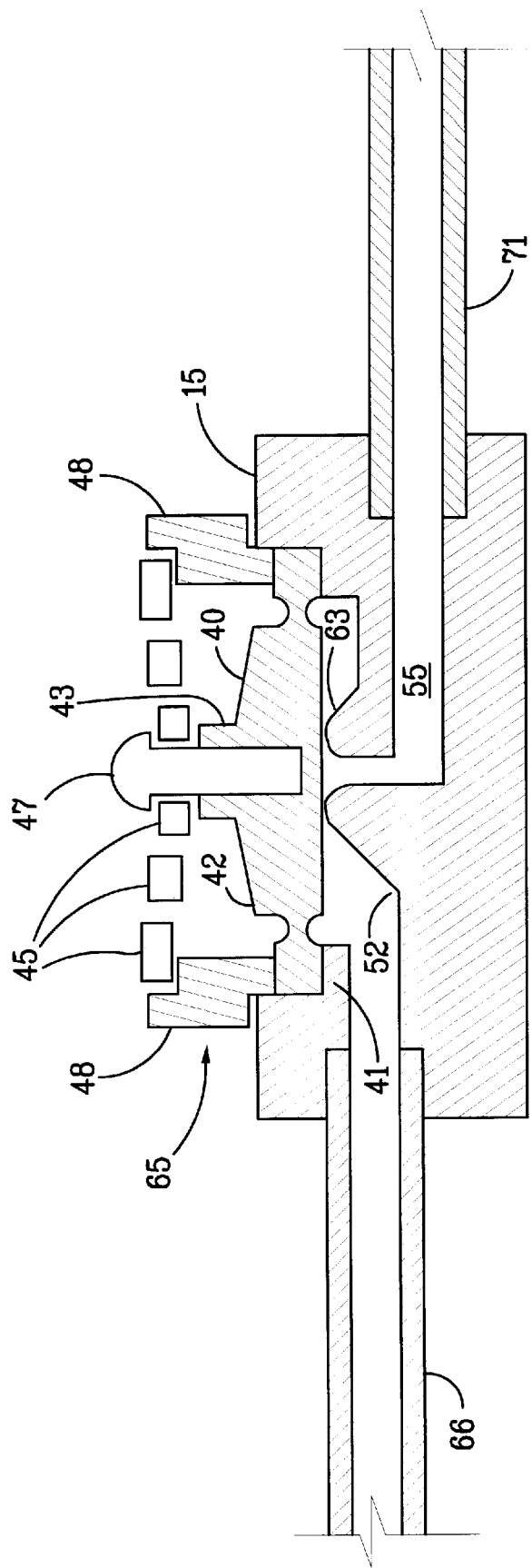
FIG. 6 is a sectional view of the regulator valve shown in FIG. 5.

There is shown in FIGS. 5 and 6 an alternative form of the wound drainage system wherein the regulator valve is constructed independent of the container wherein the wound fluid is collected. By separating the regulator valve from the container, the container can be of a simplified construction that can be effectively sterilised and therefore be re-used numerous times. This is a substantial commercial advantage compared with the integrally constructed container and regulator valve unit described with reference to FIGS. 1 to 4, which cannot be effectively sterilised, and hence must be totally discarded after a single use.

Figure 3:
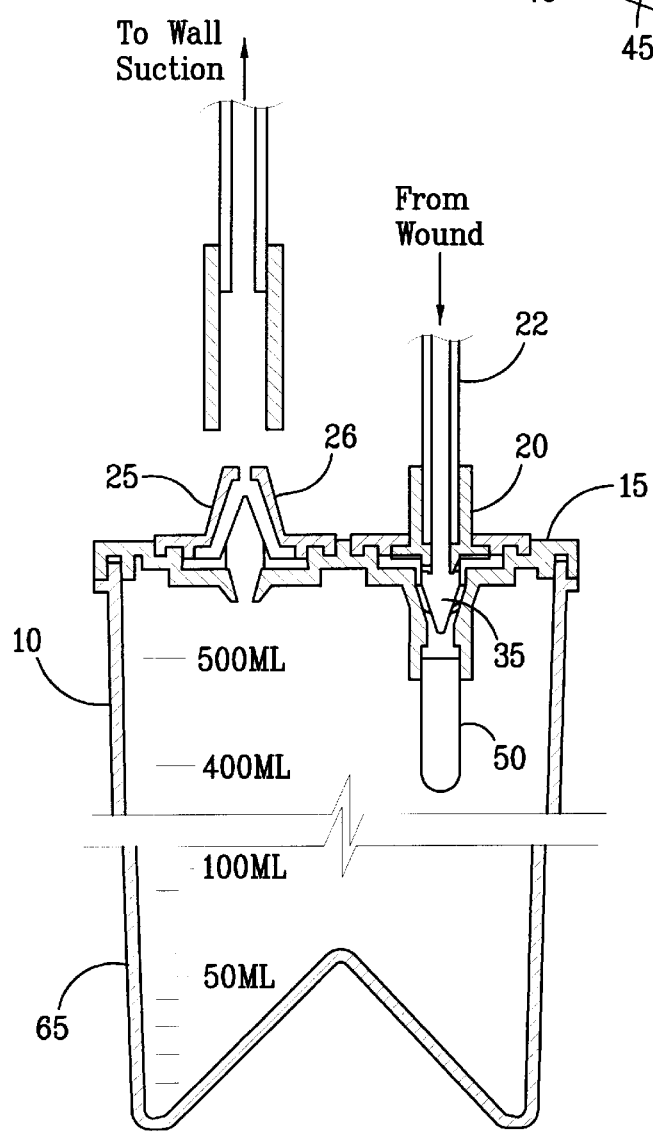
FIG. 3 is a section on line 3—3 of FIG. 2.

As seen in FIG. 5, the container 62 is of a simple cylindrical form with a removable closure 61, and may have an inverted conical base as shown in FIG. 3 in relation to the container 60. The container cap 63 is removable for discarding of the fluid collected therein and for sterilisation between successive uses. The coupling 64 provided in the cap 63 is connectable to the hospital reticulated vacuum system to enable initial establishment of the required level of vacuum in the container.

The independent regulator 65 is connected to the container 62 by the tube 71 and to the wound by a conventional wound drainage tube portion of which is shown at 66.

The construction and operation of the regulator 65 is substantially the same as the regulator 40 previously described. The regulator disc 42, compliance element 45 and screw 47, and the operation and adjustment thereof, are each identical to that previously described with reference to FIGS. 3 and 4, and have therefore been identified by the same reference numeral. The description thereof will not be repeated here. The differences from the regulator 40 reside in the wound fluid drain tube 66 being received in sealed relation in the cavity 69 to communicate with the cavity 52 immediately upstream of the valve 44. Also the passage 55, downstream of the valve 44, communicates directly with the transfer tube 71 via which wound fluid is transferred to an independent container (not shown) but would basically be the same as the container 10, but without the regulator valve incorporated therein.

This construction employing separate regulator valve and fluid collection container, providing the ability for multiple use of the container significantly improves the economics of the complete would drainage unit.

In the regulator valve described with reference to FIGS. 2, 3 and 4 or FIGS. 5 and 6, the compliant member 45 is in the form of a disk which is rotated against a circular ramp to vary the degree of flexion induced, thus exerting an upward force on the regulator valve 40. The same functional effect could also be achieved by employing other means such as:

- a compliant beam secured to the cap 48 at one end, and to the regulator valve 40 at the other, with a central screw or ramp device to lift the beam's centre point, thereby applying a controlled upward force to the regulator valve;
- a compliant beam secured to the regulator valve at one end, with a fulcrum in the centre and a screw or ramp device to press down on the other end, which would also apply a controlled upward force to the regulator valve;
- a tension spring, one end attached to the upper side of the regulator valve, the other to an adjustably moveable anchor point, allowing variable tension force to be generated in the spring, thus applying a controlled upward force to the regulator valve.

The materials envisioned for the construction of the invention would favour appropriate grades of mouldable plastics, but need not be limited to these. Other materials such as glass, metals and rubber could equally be employed as and where cost and performance dictated.

We claim:

1. A method of withdrawing fluid from a wound comprising a passage between the wound and a container with valve means to control flow of fluid from the passage to the container, said method comprising cyclically establishing in the passage a level of vacuum at or above a selected value and a higher level of vacuum in the container, drawing fluid from the wound while the valve means is closed to collect said fluid in said passage, and opening said valve means in response to the level of vacuum in said passage falling below said select value to permit discharge of fluid from said passage to the container to thereby re-establish said selected or higher level of vacuum in the passage, wherein said valve means comprises an elastomeric disc having an annular compliant section and a valve section, wherein in use said valve section releasably engages a seat in said passage.

2. A method as claimed in claim 1 wherein the selected value of level of vacuum is adjusted to control the rate of withdrawal of the fluid from the wound.

3. An apparatus for withdrawing fluid from a wound comprising a conduit to be connected at one end to a wound to receive fluid from the wound for delivery to a container, valve means to be in use selectively provide communication between the conduit and said container when connected thereto, said valve means being adopted for establishing communication between the conduit and the container in response to t he existence of a level of vacuum in said conduit below a selected value, to permit wound fluid to flow from the conduit to the container, wherein said valve means comprises an elastomeric disc having an annular compliant section and a valve section, wherein in use said valve section releasably engages a seat in said conduit.

4. An apparatus as claimed in claim 3 wherein said valve means is adapted to be detachably connectable to the container.

5. An apparatus as claimed in claim 3 wherein said valve means is detachably connectable to said container by a delivery conduit.

6. An apparatus as claimed in claim 5 wherein the conduit, valve means and delivery conduit are an integral assembly detachably connectable to the container.

7. An apparatus as claimed in any one of claims 3 to 6 wherein said valve means are adapted to permit adjustment of said selected value of the level of vacuum in the conduit, within a specific range.

8. An apparatus for withdrawing fluid from a wound comprising a conduit to be connected at one end to a wound to receive fluid from the wound and is connected at the other end to a container to deliver wound fluid to the container, valve means arranged and operable to selectively permit fluid to flow from the conduit to the container, said valve means being adopted to provide communication to permit said flow from the conduit to the container in response to the existence of a level of vacuum in said conduit upstream of the valve means below a selected value, wherein said valve means comprises an elastomeric disc having an annular compliant section and a valve section, wherein in use said valve section releasably engages a seat in said conduit.

9. An apparatus as claimed in claim 8 wherein said valve means is detachably connectable to the container.

10. An apparatus as claimed in claim 8 or 9 wherein said valve means is adapted to permit adjustment of said selected value of the level of vacuum in the conduit, within a specific range.

* * * * *

UNITED STATES PATENT AND TRADEMARK OFFICE
CERTIFICATE OF CORRECTION

PATENT NO. : 5,944,703
DATED : August 31, 1999
INVENTOR(S) : Dixon et al.

It is certified that error appears in the above-identified patent and that said Letters Patent is hereby corrected as shown below:

On the title page, at [73] Assignee, please delete "Leadersville" and insert --Leederville-- therefor.

In column 3, line 5, please delete "EMBODIMENT" and insert --INVENTION-- therefor.

In column 6, line 28, please delete "t he" and insert --the-- therefor.

Signed and Sealed this

Twenty-ninth Day of May, 2001

Attest:

NICHOLAS P. GODICI

Attesting Officer

Acting Director of the United States Patent and Trademark Office